United States Patent
Wang et al.

(10) Patent No.: US 9,464,233 B2
(45) Date of Patent: Oct. 11, 2016

(54) SILOXANE-CONTAINING TRIANHYDRIDE, POLYMER, LIQUID CRYSTAL ALIGNMENT AGENT, LIQUID CRYSTAL ALIGNMENT FILM, AND LIQUID CRYSTAL DISPLAY DEVICE

(71) Applicant: Daxin Materials Corporation, Taichung (TW)

(72) Inventors: Po-Yang Wang, Taichung (TW); Yi-Chun Lin, Taichung (TW); Min-Ruei Tsai, Taichung (TW)

(73) Assignee: Daxin Materials Corporation, Taichung (TW)

( * ) Notice: Subject to any disclaimer, the term of this patent is extended or adjusted under 35 U.S.C. 154(b) by 0 days.

(21) Appl. No.: 14/640,025

(22) Filed: Mar. 6, 2015

(65) Prior Publication Data
US 2015/0252266 A1    Sep. 10, 2015

(30) Foreign Application Priority Data

Mar. 7, 2014    (TW) .............. 103107949 A

(51) Int. Cl.
| | | |
|---|---|---|
| C09K 19/56 | (2006.01) | |
| C07F 7/08 | (2006.01) | |
| C08G 73/10 | (2006.01) | |
| C08J 5/18 | (2006.01) | |
| G02F 1/1337 | (2006.01) | |
| C07F 7/18 | (2006.01) | |
| C09D 179/08 | (2006.01) | |
| C08G 77/14 | (2006.01) | |
| C08G 77/455 | (2006.01) | |
| C08G 77/04 | (2006.01) | |
| C08G 77/38 | (2006.01) | |

(52) U.S. Cl.
CPC .............. *C09K 19/56* (2013.01); *C07F 7/0852* (2013.01); *C07F 7/1836* (2013.01); *C08G 73/106* (2013.01); *C08G 73/1042* (2013.01); *C08G 73/1075* (2013.01); *C08G 77/045* (2013.01); *C08G 77/14* (2013.01); *C08G 77/38* (2013.01); *C08G 77/455* (2013.01); *C08J 5/18* (2013.01); *C09D 179/08* (2013.01); *G02F 1/133723* (2013.01); *C08J 2379/08* (2013.01); *G02F 1/133711* (2013.01)

(58) Field of Classification Search
CPC .......... C09K 19/56; C08J 5/18; C08G 77/455
See application file for complete search history.

(56) References Cited

U.S. PATENT DOCUMENTS

| | | | |
|---|---|---|---|
| 4,381,396 A | 4/1983 | Ryang | |
| 4,794,153 A | 12/1988 | Rich | |
| 5,627,253 A | 5/1997 | Nakashima | |
| 6,500,976 B2 | 12/2002 | Matsuda et al. | |
| 2001/0049428 A1* | 12/2001 | Okawa ................ | C08G 77/388 528/38 |

FOREIGN PATENT DOCUMENTS

| | | |
|---|---|---|
| TW | 201109368 | 3/2011 |
| TW | I367233 | 7/2012 |

* cited by examiner

*Primary Examiner* — Kuo-Liang Peng
(74) *Attorney, Agent, or Firm* — Jianq Chyun IP Office

(57) ABSTRACT

Provided is a siloxane-containing trianhydride having a structure shown in formula 1:

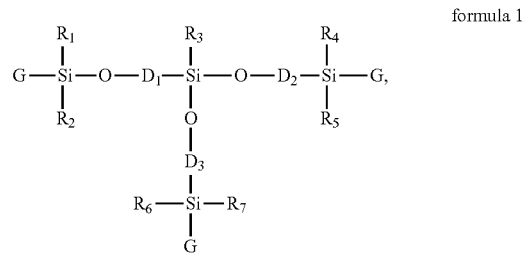

wherein
$R_1$ to $R_7$, $D_1$ to $D_3$, and each G are as defined in the specification.

12 Claims, 1 Drawing Sheet

SILOXANE-CONTAINING TRIANHYDRIDE, POLYMER, LIQUID CRYSTAL ALIGNMENT AGENT, LIQUID CRYSTAL ALIGNMENT FILM, AND LIQUID CRYSTAL DISPLAY DEVICE

CROSS-REFERENCE TO RELATED APPLICATION

This application claims the priority benefit of Taiwan application serial no. 103107949, filed on Mar. 7, 2014. The entirety of the above-mentioned patent application is hereby incorporated by reference herein and made a part of this specification.

BACKGROUND OF THE INVENTION

1. Field of the Invention

The invention relates to an anhydride compound, and more particularly, to a siloxane-containing trianhydride, a polymer obtained by performing a polymerization reaction using the siloxane-containing trianhydride as raw material, a liquid crystal alignment agent and a liquid crystal alignment film containing the polymer, and a liquid crystal display device having the liquid crystal alignment film.

2. Description of Related Art

In recent years, in various flat panel display devices, the liquid crystal display device has become the mainstream product in the market due to advantages such as small size, thin and light frame, power save, low power consumption, and good display quality.

The operating principle of the liquid crystal display device is based on the adjustment of voltage applied on the liquid crystal display device to change the arrangement of liquid crystal molecules. As a result, the polarization direction of light passing through the liquid crystal molecules is influenced such that the liquid crystal display device shows a change in brightness. In particular, the basic structure of the liquid crystal display device includes two transparent electrically conductive substrates. Liquid crystal is injected between the substrates, and a polarizer is added to the outside of each of the two substrates. Moreover, to arrange the liquid crystal molecules at a predetermined tilt angle in a specific direction, a layer of liquid crystal alignment film is coated on each of the two substrates, and rubbing is performed by applying pressure with a soft cloth such as cotton or nylon such that a nano-scale trench is left on each of the films. As a result, liquid crystal molecules can be arranged in each of the trenches in a fixed and uniform direction via an interaction force with polymers of each of the films such that a stable tilt angle is achieved.

The liquid crystal alignment agent material forming the liquid crystal alignment film can be a polymer such as polyamic acid, polyimide, polyester, or poly-organosiloxane, wherein polyimide is the most used liquid crystal alignment agent material due to properties such as chemical stability and thermal stability.

Since the demand for display quality of the liquid crystal display device is constantly increasing, the development of the material of the liquid crystal alignment agent is also becoming more important.

SUMMARY OF THE INVENTION

Technical Issue to be Solved

The invention provides a siloxane-containing trianhydride, a polymer obtained by performing a polymerization reaction using the siloxane-containing trianhydride as raw material, a liquid crystal alignment agent and a liquid crystal alignment film containing the polymer, and a liquid crystal display device having the liquid crystal alignment film. Via the siloxane-containing trianhydride having a novel structure, the invention provides a brand new raw material for the liquid crystal alignment film such that those skilled in the art are no longer limited to synthesizing polyamic acid and/or polyimide with tetracarboxylic dianhydride and diamine. At the same time, the liquid crystal display device of the invention further shows superior electrical properties.

Technical Solution

The siloxane-containing trianhydride of the invention has a structure shown in formula 1:

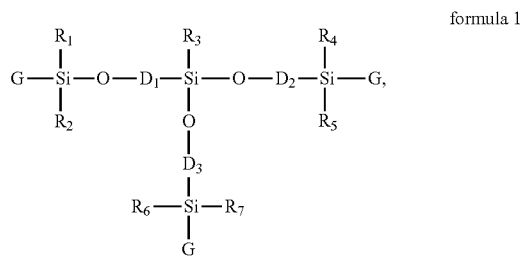

formula 1 wherein each G is independently a group derived from compounds a to j:

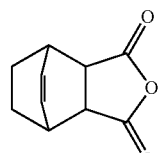

a

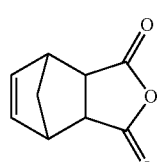

b

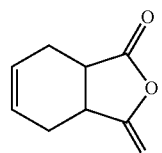

c

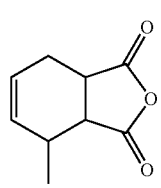

d

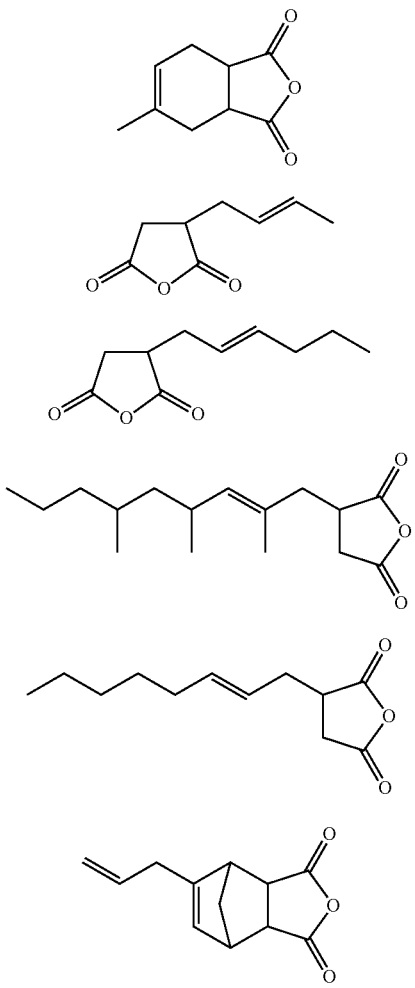

$R_1$ to $R_7$ are each independently an alkyl group or a phenyl group, and $D_1$ to $D_3$ are each independently $-(R_aR_bSiO)_n-$, wherein $R_a$ and $R_b$ are respectively an alkyl group or a phenyl group, and n is an integer of 0 to 3.

In an embodiment, n is 0.

In an embodiment, at least one of $R_a$, $R_b$ and $R_1$ to $R_7$ is a phenyl group and the rest are each independently a $C_1$ to $C_3$ alkyl group.

In an embodiment, $R_3$ is a phenyl group, and $R_a$, $R_b$, $R_1$, $R_2$, $R_4$, $R_5$, $R_6$, and $R_7$ are each independently a methyl group.

The polymer of the invention includes a unit represented by formula 2 or a unit represented by formula 3:

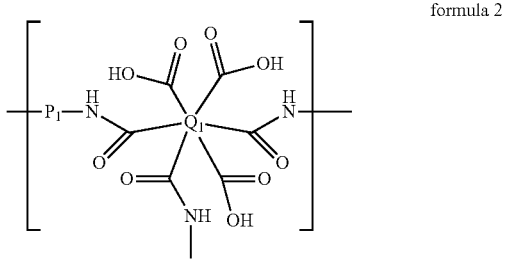

formula 2

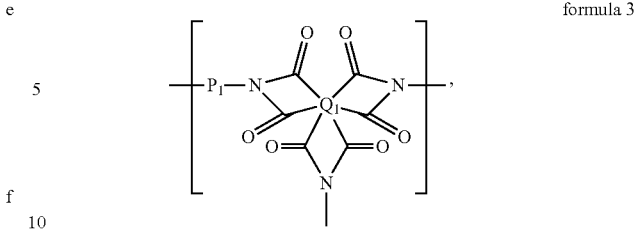

formula 3 wherein $P_1$ is a diamine residue and $Q_1$ is a residue of a siloxane-containing trianhydride, and the siloxane-containing trianhydride has the structure shown in formula 1.

In an embodiment of the invention, the ratio of the unit represented by formula 2 and the unit represented by formula 3 in the polymer is 10 mol % to 99 mol %, preferably 30 mol % to 99 mol %, and more preferably 70 mol % to 99 mol %.

The liquid crystal alignment agent of the invention contains the polymer.

The liquid crystal alignment film of the invention contains the polymer.

The liquid crystal display device of the invention contains the liquid crystal alignment film.

Beneficial Effects

Based on the above, the invention provides a siloxane-containing trianhydride, a polymer synthesized by using the siloxane-containing trianhydride as raw material, and a liquid crystal alignment agent, a liquid crystal alignment film and a liquid crystal display device containing the polymer. When the liquid crystal alignment film has a structure derived from the siloxane-containing trianhydride, the voltage holding ratio of the liquid crystal display device is increased. As a result, the performance of the liquid crystal display device is improved.

To make the above features and advantages of the invention more comprehensible, several embodiments are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
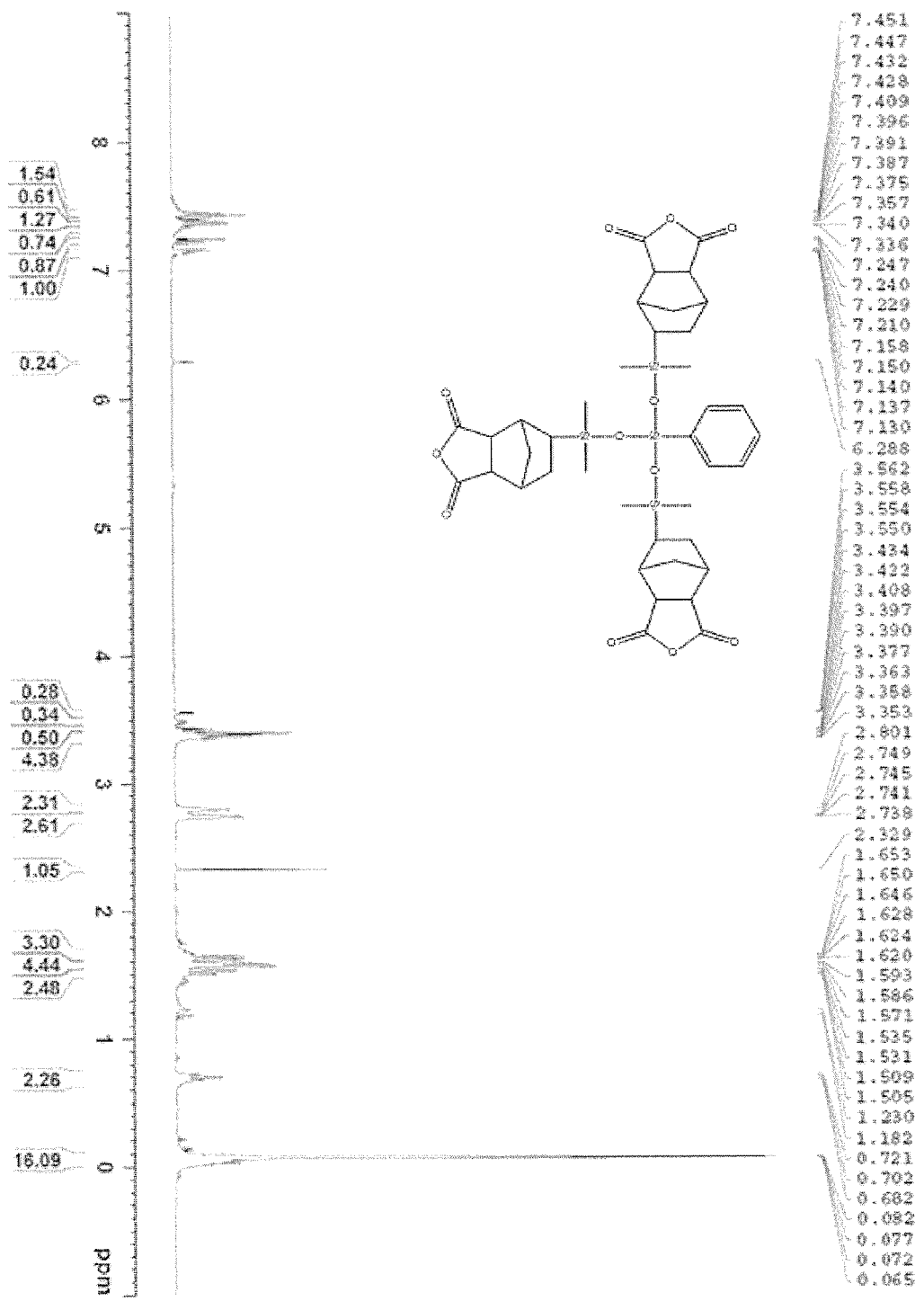
FIG. 1 is the NMR spectrum of a siloxane-containing trianhydride of the synthesis example.

In the present specification, a range represented by "a numerical value to another numerical value" is a schematic representation for avoiding listing all of the numerical values in the range in the specification. Therefore, the recitation of a specific numerical range discloses any numerical value in the numerical range and a smaller numerical range defined by any numerical value in the numerical range, as is the case with the any numerical value and the smaller numerical range stated expressly in the specification. For instance, the range of "10 mol % to 99 mol %" discloses the range of "20 mol % to 50 mol %", regardless of whether other numerical values are listed in the specification.

In the present text, if it is not particularly specified whether a group is substituted, then the group can represent a substituted or an unsubstituted group. For instance, "alkyl group" can represent a substituted or an unsubstituted alkyl group.

In the present text, skeleton formulas are sometimes used to represent compound structures. Such representation can omit carbon atoms, hydrogen atoms, and carbon-hydrogen bonds. Of course, structural formulas with clear illustrations of atoms or atomic groups are definitive.

The first embodiment of the invention relates to a siloxane-containing trianhydride, and the structure thereof is as shown in formula 1:

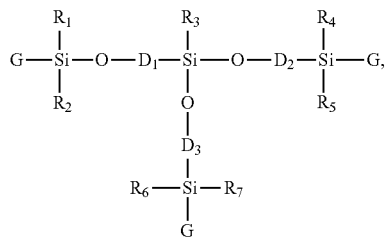

formula 1 wherein
each G is independently a group derived from compounds a to j:

a
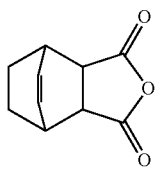

b
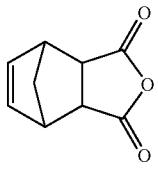

c
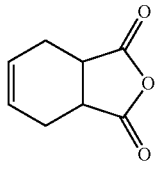

d
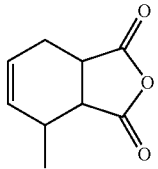

e
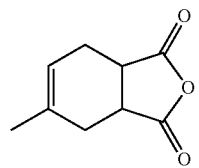

f
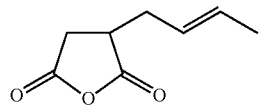

g
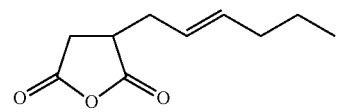

h
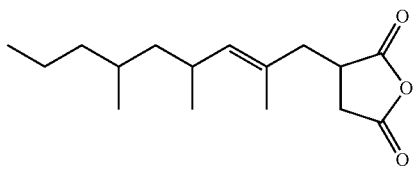

i
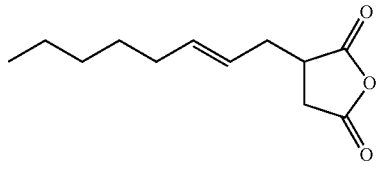

j
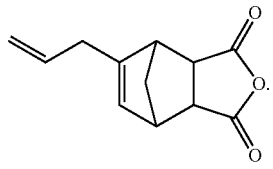

Here, the so-called "G is derived from compounds a to j" means that G is a monovalent group derived from a reaction generated between compounds a to j and a siloxane compound via an olefinic bond of compounds a to j. Using compound b as an example, G can be

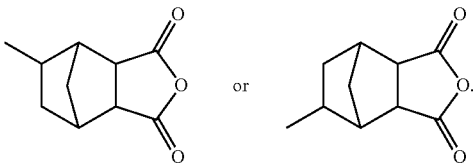

$R_1$ to $R_7$ of formula 1 are each independently an alkyl group or a phenyl group, wherein the alkyl group can be a $C_1$ to $C_3$ alkyl group, and the phenyl group can be an unsubstituted phenyl group.

$D_1$ to $D_3$ of formula 1 are each independently $-(R_aR_b\text{-}SiO)_n-$, wherein $R_a$ and $R_b$ are respectively an alkyl group or a phenyl group, the alkyl group can be a $C_1$ to $C_3$ alkyl group and n is an integer of 0 to 3. In the technical art of the present application, $D_1$ to $D_3$ are also sometimes called D units (difunctional siloxane units), and the lower limit of n is zero, that is, the structure shown in formula 1 may not contain D units.

In an embodiment, $R_3$ is a phenyl group, and $R_a$ and $R_b$ (in the case that n is not equal to 0) are each independently a methyl group, and $R_1$, $R_2$, $R_4$, $R_5$, $R_6$, and $R_7$ are also each independently a methyl group.

The siloxane-containing trianhydride represented by formula 1 can be obtained via a hydrosilation reaction between a siloxane compound having a terminal Si—H bond and compounds a to j. The siloxane compound having the terminal Si—H bond can be represented by, for instance, formula 1-1:

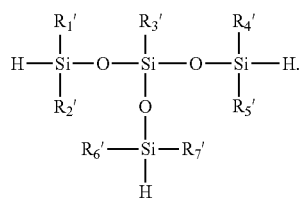

formula 1-1

In particular, the definition of each of $R_1'$ to $R_7'$ is respectively the same as that of each of $R_1$ to $R_7$.

Accordingly, the siloxane-containing trianhydride for which n is equal to 0 in formula 1 can be obtained.

Alternatively, D units can also be connected to the terminal of a siloxane compound shown in formula 1-2 via a dehydration condensation reaction to form a siloxane compound shown in formula 1-3. Here, the raw material of each of the D units can be a siloxane compound having a silanol group (Si—OH) at a terminal and a Si—H bond at another terminal. Then, the siloxane compound represented by formula 1-3 is reacted with compounds a to j via a hydrosilation reaction to obtain the siloxane-containing trianhydride for which n is not equal to 0 in formula 1.

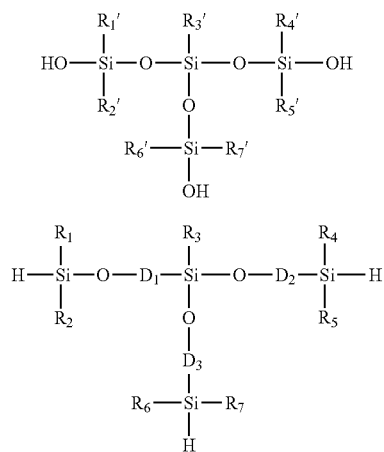

The hydrosilation reaction and the dehydration condensation reaction are known in related technical art, and those skilled in the art can select a suitable raw material and adjust reaction conditions according to related literature.

The siloxane-containing trianhydride of the first embodiment can be reacted with a diamine to form a polyimide compound (i.e., a polymer having an amide bond and/or an imide bond such as polyamic acid, polyimide, or polyamic acid-polyimide). Therefore, the invention further includes another (second) embodiment for a polymer including a unit represented by formula 2 or a unit represented by formula 3:

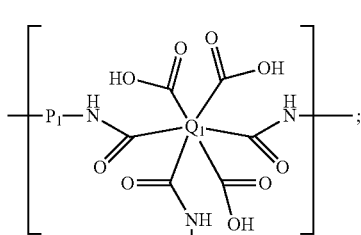

formula 2

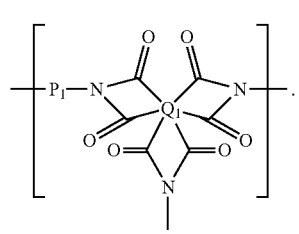

formula 3

In formula 2 and formula 3, $P_1$ is a diamine residue and $Q_1$ is a residue of a siloxane-containing trianhydride, and the siloxane-containing trianhydride has the structure shown in formula 1.

Here, the so-called "diamine residue" refers to a divalent group obtained by removing every —$NH_2$ group from the diamine compound, and the so-called "residue of siloxane-containing trianhydride" refers to a hexavalent group obtained by removing every anhydride structure (—(CO)O (CO)—) from the siloxane-containing trianhydride.

It should be mentioned that, if the polymer is formed by the unit shown in formula 2, then the combination of units is achieved by connecting a $P_1$ group and a nitrogen atom located on the right side and the lower side of formula 2. Similarly, when the polymer includes the unit shown in formula 3, or includes the unit of formula 2 and the unit of formula 3 at the same time, or even further includes other units, the method of combining each unit is the same as above.

The synthesis method of the polymer of the second embodiment is exemplified below. First, the unit shown in formula 2 can be obtained by reacting the siloxane-containing trianhydride shown in formula 1 and a diamine compound ($H_2N$—$P_1$—$NH_2$). Here, the diamine compound is not particularly limited. Any diamine compound capable of being reacted with an anhydride can be used. Specifically, the diamine compound can be the diamine compounds recited in Table 2 and Table 3 in ROC Patent Publication No. I367233, the entire content of which is incorporated into the present application as the basis for modifications and description of the present application.

The reaction between the siloxane-containing trianhydride and the diamine can be completed in an organic solvent. The organic solvent used can be divided into an organic solvent having better solubility and an organic solvent having worse solubility. The organic solvent having better solubility includes, for instance, N-methyl-2-pyrrolidone, N,N-dimethylformamide, N,N-dimethylacetamide, N-methyl caprolactam, dimethyl sulfoxide, tetramethyl urea, hexamethylphosphoric amide, γ-butyrolactone, or pyridine. The solvents can be used in combination. In addition to the solvents, any solvent capable of dissolving the formed polymer can be used.

The organic solvent having worse solubility can also be used in combination with the organic solvent having better solubility, provided that the formed polymer is not separated. The organic solvent having worse solubility includes, for instance, methanol, ethanol, isopropanol, n-butanol, cyclohexanol, ethylene glycol, ethylene glycol monomethyl ether, ethylene glycol monoethyl ether, ethylene glycol monobutyl ether, ethylene glycol dimethyl ether, ethylene glycol diethyl ether, diethyl ether, acetone, methyl ethyl ketone, cyclohexanone, methyl acetate, ethyl acetate, tetrahydrofuran, dichloromethane, trichloromethane, 1,2-dichloroethane, benzene, toluene, xylene, n-hexane, n-heptane, or n-octane.

The unit shown in formula 3 is a product obtained after the dehydration cyclization of the unit shown in formula 2.

The dehydration cyclization reaction can be performed via (1) direct heating or (2) addition of a dehydrating agent and a catalyst.

(1): the temperature of the heating dehydration cyclization reaction is preferably 50° C. to 300° C., more preferably 100° C. to 250° C. When the reaction temperature is lower than 50° C., the dehydration cyclization reaction is not performed.

(2): the temperature for performing a dehydration cyclization reaction via the addition of a dehydrating agent and a catalyst is preferably −20° C. to 150° C., more preferably 0° C. to 120° C. The dehydrating agent can include an anhydride such as acetic anhydride, propionic anhydride, or trifluoroacetic anhydride, and the usage amount thereof is decided according to the needed imidization ratio. The catalyst can include a tertiary amine such as triethylamine, pyridine, or lutidine, and the usage amount thereof is preferably 0.01 moles to 10 moles per mole of dehydrating agent.

In addition to the unit represented by each of formula 2 and formula 3, the polymer of the present embodiment can also include a unit represented by formula 4 and/or a unit represented by formula 5:

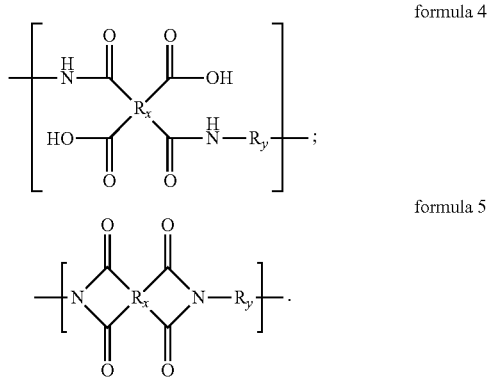

In particular, $R_x$ is a residue of tetracarboxylic dianhydride, and $R_y$ is a residue of diamine. Here, the definition of "residue" is as described above. Here, the tetracarboxylic dianhydride is not particularly limited, and any tetracarboxylic dianhydride capable of being reacted with an amine group to produce a carboxyl group and an amide group can be used. Specific examples of the tetracarboxylic dianhydride can include, for instance, the compounds shown in Table 1 of ROC Patent No. I367233. Here, the diamine can be the same as described above.

Formula 4 shows a unit of polyamic acid produced from a reaction of tetracarboxylic dianhydride and diamine, and formula 5 shows a product of dehydration cyclization of the unit of formula 4. The reactions are known to those skilled in the art and are not repeated herein.

The ratio of the unit represented by formula 2 and the unit represented by formula 3 in the polymer of the second embodiment is not particularly limited. The lower limit thereof is, for instance, 0.1 mol % or 1 mol %, and the upper limit thereof is, for instance, 60 mol % or 20 mol %.

The polymer of the second embodiment can be used as the material of the liquid crystal alignment film in the liquid crystal display device. Therefore, the invention further includes different embodiments for the liquid crystal alignment agent, the liquid crystal alignment film, and the liquid crystal display device, wherein the liquid crystal alignment agent and the liquid crystal alignment film include the polymer of the second embodiment, and the liquid crystal display device includes the liquid crystal alignment film.

The third embodiment of the invention relates to a liquid crystal alignment agent including the polymer of the second embodiment dissolved in a solvent. The solvent includes, for instance: N-methyl-2-pyrrolidone, N,N-dimethylformamide, N,N-dimethylacetamide, N-methyl caprolactam, dimethyl sulfoxide, γ-butyrolactone, γ-butyrolactam, ethylene glycol monomethyl ether, ethylene glycol monoethyl ether, ethylene glycol mono-n-propyl ether, or ethylene glycol monobutyl ether. The solvents can be used in combination.

Moreover, if needed, the liquid crystal alignment agent can further include, for instance, an organosilane/organosiloxane compound, an epoxy compound, or other additives.

The fourth embodiment of the invention relates to a liquid crystal alignment film including the polymer of the second embodiment, and can be fabricated with the liquid crystal alignment agent of the third embodiment. The fabrication method thereof includes, in short, coating the liquid crystal alignment agent on a substrate, and then removing the solvent via heating to form a film. Here, if the solid content of the liquid crystal alignment agent is lower than 1 wt %, then the film thickness of the coated alignment film may be too small such that liquid crystal alignment is reduced; and if the solid content of the liquid crystal alignment agent is greater than 10 wt %, then coating quality is affected. Based on the above factors, the solid content of the liquid crystal alignment agent is preferably 1 wt % to 10 wt %.

The fifth embodiment of the invention relates to a liquid crystal display device including the above liquid crystal alignment film and can be obtained by, for instance, the following method:

(1) A liquid crystal alignment agent is coated on a glass substrate having a patterned transparent conductive film via a roll coating method, a spin coating method, or a printing method. Then, heat baking is performed to form a thin film. The main purpose of heat baking is to remove the organic solvent in the liquid crystal alignment agent and promote the dehydration cyclization of the unit of formula 2 and the unit of formula 4 (if present). The temperature of the heat baking can be 80° C. to 300° C., preferably 100° C. to 240° C. The thickness of the formed thin film is preferably 0.005 microns to 0.5 microns.

(2) Optionally, a rubbing process can be performed, in a fixed direction, on the formed thin film via a roller on which nylon or cotton fiber cloth is wrapped. Via the step, the alignment film can provide alignment to liquid crystal molecules.

(3) A sealant is coated on the substrate having a liquid crystal alignment film, and a spacer is sprayed on the other substrate having a liquid crystal alignment film. Then, the two liquid crystal alignment film substrates are combined in a manner in which the rubbing directions are perpendicular to each other or parallel to each other. Thereafter, liquid crystal is injected into the gap between the substrates, and the injection hole is sealed, thus forming a liquid crystal display device.

Due to the characteristics of the Si—O bond, in comparison to the known liquid crystal alignment film containing a polyimide compound, the liquid crystal alignment film containing the polymer of the second embodiment has lower chemical activity, and better thermal stability and electrical insulation. Therefore, higher voltage holding ratio (VHR) can be achieved.

Moreover, to satisfy different functional demands of the liquid crystal alignment film, the liquid crystal alignment film can contain more than one polymer. For instance, one of the polymers is used to adjust electrical properties, and another one is used to adjust the tilt angle of the liquid crystal. If the various polymers are mixed together, then the intended use of each thereof may not be achieved. To promote the separation of different polymers, after the liquid crystal alignment agent is coated on the substrate, baking is generally performed at a higher temperature such that the polymers are closer to a melted state. However, in this case, more energy is consumed, and the cost is correspondingly increased. In this regard, due to the characteristics of the Si—O bond, the polarity of the polymer of the second embodiment is relatively low, and when mixed with other polyimide compounds, the polymer is more readily separated from the other polyimide compounds, thus reducing the temperature of the baking process (for instance, the baking temperature can be reduced from 230° C. to 200° C.). Alternately, from another perspective, better separation effect can be achieved under the same baking temperature.

Experiments

Examples are provided below to more specifically describe the invention. Although the following experiments are described, the materials used and the amount and ratio of each thereof, as well as treatment details and treatment procedures . . . etc., can be suitably modified without exceeding the scope of the invention. Accordingly, restrictive interpretation should not be made to the invention based on the experiments described below.

Synthesis of siloxane-containing trianhydride: in the synthesis example, the raw materials of the reaction are as follows:

Siloxane-containing compound A:

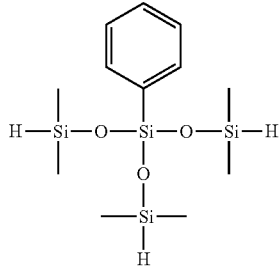

Andydride compound B:

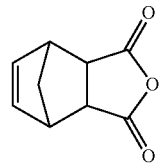

49.25 g of 5-Norbornene-2,3-dicarboxylic anhydride (i.e., anhydride compound B; CAS: 826-62-0) was mixed in 41.16 g of toluene, then 0.01 g of PC085 (Pt Cyclic Silicone (Ashbey's catalyst) catalyst produced by UCT Corporation) was added, and then the mixture was uniformly stirred. After the temperature was raised to 110° C., the mixture was left at 110° C. for 8 hours. Then, the temperature was reduced to 90° C., and then 34.72 g of phenyltris(dimethylsiloxy)silane (i.e., siloxane compound A; CAS: 18027-45-7) was added. The mixture was left at 90° C. for 12 hours, and the IR spectrum of the reactants was observed. The starting material phenyltris(dimethylsiloxy)silane has a strong Si—H signal at 2132.70 cm$^{-1}$. After the reaction was complete, the Si—H signal of the starting material phenyltris(dimethylsiloxy)silane disappeared. At this point, toluene was drained to obtain a siloxane-containing trianhydride compound having a yield of 98%. The structure and the NMR spectrum of the product are as shown in FIG. 1, and the structure is equivalent to a structure for which, in formula 1, $R_3$ is an unsubstituted phenyl group, $R_1$ to $R_7$ are each independently an unsubstituted methyl group, and n is 0. In the following, abbreviation THNA refers to the siloxane-containing trianhydride product.

Synthesis of polymer I: various diamine monomers (3CC, AP, TMDA) were mixed in 200 g of N-methyl-2-pyrrolidone (NMP) in specific usage amounts, and then the mixture was stirred for 30 minutes. Then, the siloxane-containing trianhydride monomer THNA was added, and then a polymerization reaction of the THNA and the diamines was performed at 25° C. for 40 minutes. Then, BT-100 was added, and then a polymerization reaction was performed at 25° C. for 8 hours. After 8 hours, dehydration cyclization was performed with toluene. Then, after the temperature was reduced, CBDA was added in a specific ratio, and then NMP was added to adjust the solid content of all of the reactants to 15 wt %. A polymerization reaction was performed by continuously stirring at 25° C. for 8 hours. As a result, a polyimide and polyamic acid copolymer solution having a solid content of 15 wt % was obtained. The additive amount of each of the various starting materials and the abbreviation of each of the various compounds are as shown in Table 1 and footnotes thereof.

Synthesis of polymer II: 200 mmole of diamine monomer TMDA was added to 200 g of NMP, the mixture was stirred for 30 minutes, then 200 mmole of CBDA was added, and then NMP was added to adjust the solid content of all of the reactants to 15 wt %. Then, the mixture was continuously stirred at 25° C. for 8 hours to perform a polymerization reaction, thus obtaining a polyamic acid polymer solution having a solid content of 15 wt %.

Fabrication of the liquid crystal alignment agent, the liquid crystal alignment film, and the liquid crystal display device: using NMP/diethyleneglycol monobutyl ether (BC) (weight ratio=1:1) as a mixed solvent, the obtained polyimide and polyamic acid copolymer solution and/or polyamic acid polymer solution were mixed according to a specific ratio (see Table 1), and then the mixture was diluted to a solid content of 6.5 wt % to obtain a liquid crystal alignment agent. Then, the liquid crystal alignment agent was coated on a glass substrate to form a thin film having a thickness of 1200±100 Å, and then the thin film was baked at 230° C. for 30 minutes to form a liquid crystal alignment film. Lastly, a pair of substrates on which the above liquid crystal alignment film was formed was combined with a liquid crystal (model: LCT-11506, obtainable from AUO) via a known method to obtain liquid crystal display devices D1 to D12 containing a pair of liquid crystal alignment films, a liquid crystal layer sandwiched between the liquid crystal alignment films, and a pair of electrode layers respectively disposed on the side of each of the pair of liquid crystal alignment films away from the liquid crystal layer.

Measurement conditions of VHR: under an ambient temperature of 60° C., direct current (1V or 5V, 0.6 Hz, pulse width: 60 μsec) was applied to each of the liquid crystal display devices, and then the VHR of each of the liquid crystal display devices was measured. The results thereof are presented in the last column of Table 1.

TABLE 1

| | Device | Polymer I | | | | | | Polymer II | | Ratio (wt %) | Property measurement | |
| | | 3CC (mmole) | AP (mmole) | TMDA (mmole) | THNA (mmole) | BT-100 (mmole) | CBDA (mmole) | TMDA (mmole) | CBDA (mmole) | Polymer I/ Polymer II | 1V-VHR (%) | 5V-VHR (%) |
|---|---|---|---|---|---|---|---|---|---|---|---|---|
| Example 1 | D1 | 60 | 30 | 110 | 10 | 150 | 40 | 200 | 200 | 100/0 | 83.5 | 95.3 |
| Example 2 | D2 | 70 | 30 | 100 | 10 | 150 | 40 | 200 | 200 | 100/0 | 86.7 | 96.5 |
| Example 3 | D3 | 60 | 30 | 110 | 20 | 140 | 40 | 200 | 200 | 100/0 | 84.4 | 95.4 |
| Example 4 | D4 | 70 | 30 | 100 | 20 | 140 | 40 | 200 | 200 | 100/0 | 85.6 | 96.2 |
| Example 5 | D5 | 60 | 30 | 110 | 10 | 150 | 40 | 200 | 200 | 50/50 | 81.7 | 92.8 |
| Example 6 | D6 | 70 | 30 | 100 | 10 | 150 | 40 | 200 | 200 | 50/50 | 81.9 | 92.8 |
| Example 7 | D7 | 60 | 30 | 110 | 20 | 140 | 40 | 200 | 200 | 50/50 | 86.1 | 94.1 |
| Example 8 | D8 | 70 | 30 | 100 | 20 | 140 | 40 | 200 | 200 | 50/50 | 85.0 | 93.7 |
| Comparative example 1 | D9 | 60 | 30 | 110 | — | 160 | 40 | 200 | 200 | 100/0 | 77.8 | 90.4 |
| Comparative example 2 | D10 | 70 | 30 | 100 | — | 160 | 40 | 200 | 200 | 100/0 | 78.6 | 91.8 |
| Comparative example 3 | D11 | 60 | 30 | 110 | — | 160 | 40 | 200 | 200 | 50/50 | 77.0 | 92.1 |
| Comparative example 4 | D12 | 70 | 30 | 100 | — | 160 | 40 | 200 | 200 | 50/50 | 75.6 | 91.0 |

3CC: propyl dicyclopropyl 3,5-diamino-2-methyl benzoate, made by Daxin Materials.
AP: 4-(4-phenylpiperazin-1-yl)benzene-1,3-diamine, made by Daxin Materials.
TMDA: 5(6)-amino-1,3,3-trimethyl-1-(4-aminophenyl)-indan; CAS: 54628-89-6, purchased from Chingtide.
THNA: siloxane-containing trianhydride fabricated in synthesis example.
BT-100: 1,2,3,4-butanetetracarboxylic dianhydride; CAS: 4534-73-0, purchased from Chingtide.
CBDA: 1,2,3,4-cyclobutane tetracarboxylic dianhydride, made by Daxin Materials.

It can be seen from Table 1 that, in a similar case in which the liquid crystal alignment film only contains one polymer, the liquid crystal display device of each of examples 1 to 4 shows superior VHR to the liquid crystal display device of each of comparative examples 1 and 2. Moreover, in a similar case in which the liquid crystal alignment film contains two polymers, the liquid crystal display device of each of examples 5 to 8 shows superior VHR to the liquid crystal display device of each of comparative examples 3 and 4.

Based on the above, the invention provides a siloxane-containing trianhydride, a polymer synthesized by using the siloxane-containing trianhydride as raw material, and a liquid crystal alignment agent, a liquid crystal alignment film, and a liquid crystal display device containing the polymer. When the liquid crystal alignment film has a structure derived from the siloxane-containing trianhydride, the VHR of the liquid crystal display device is increased. As a result, the performance of the liquid crystal display device is improved.

Although the invention has been described with reference to the above embodiments, the invention is not limited thereto. It will be apparent to one of the ordinary skill in the art that modifications to the described embodiments may be made without departing from the spirit of the invention. Accordingly, the scope of the invention is defined by the attached claims and not by the above detailed descriptions.

What is claimed is:

1. A siloxane-containing trianhydride, having a structure shown in formula 1:

formula 1

$$G-\underset{R_2}{\overset{R_1}{\underset{|}{\overset{|}{Si}}}}-O-D_1-\underset{\underset{D_3}{\overset{|}{\underset{|}{O}}}}{\overset{R_3}{\underset{|}{\overset{|}{Si}}}}-O-D_2-\underset{R_5}{\overset{R_4}{\underset{|}{\overset{|}{Si}}}}-G,$$

$$R_6-\underset{G}{\overset{|}{\underset{|}{Si}}}-R_7$$

wherein each G is independently a group derived from compounds a to j:

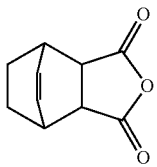
a

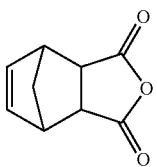
b

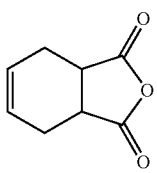
c

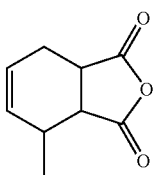
d

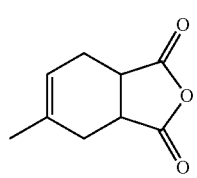
e

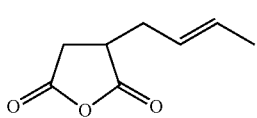
f

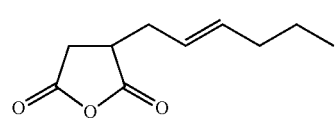
g

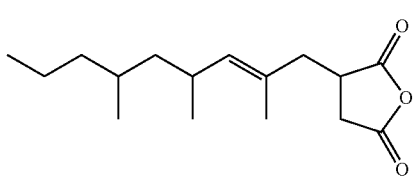
h

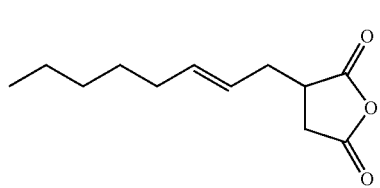
i

-continued

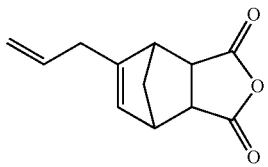
j $R_1$ to $R_7$ are each independently an alkyl group or a phenyl group, $D_1$ to $D_3$ are each independently $-(R_a R_b SiO)_n-$, wherein $R_a$ and $R_b$ are respectively an alkyl group or a phenyl group, and n is an integer of 0 to 3.

2. The siloxane-containing trianhydride of claim 1, wherein n is 0.

3. The siloxane-containing trianhydride of claim 1, wherein at least one of $R_a$, $R_b$ and $R_1$ to $R_7$ is a phenyl group and the rest are each independently a $C_1$ to $C_3$ alkyl group.

4. The siloxane-containing trianhydride of claim 1, wherein $R_3$ is a phenyl group, and $R_a$, $R_b$, $R_1$, $R_2$, $R_4$, $R_5$, $R_6$, and $R_7$ are each independently a methyl group.

5. A polymer, comprising a unit represented by formula 2 or a unit represented by formula 3:

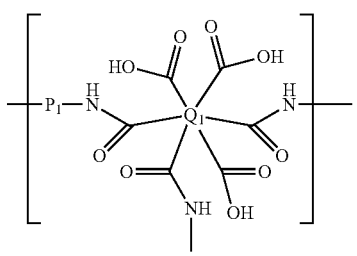

formula 2

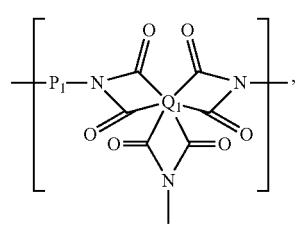

formula 3 wherein $P_1$ is a diamine residue and $Q_1$ is a residue of the siloxane-containing trianhydride of claim 1.

6. The polymer of claim 5, wherein n is 0.

7. The polymer of claim 5, wherein at least one of $R_a$, $R_b$ and $R_1$ to $R_7$ is a phenyl group and the rest are each independently a $C_1$ to $C_3$ alkyl group.

8. The polymer of claim 5, wherein $R_3$ is a phenyl group, and $R_a$, $R_b$, $R_1$, $R_2$, $R_4$, $R_5$, $R_6$, and $R_7$ are each independently a methyl group.

9. The polymer of claim 5, wherein a ratio of the unit represented by formula 2 and the unit represented by formula 3 in the polymer is 10 mol % to 99 mol %.

10. A liquid crystal alignment agent, containing the polymer of claim 5.

11. A liquid crystal alignment film, containing the polymer of claim 5.

12. A liquid crystal display device, containing the liquid crystal alignment film of claim 11.

* * * * *